United States Patent [19]

Reinehr et al.

[11] Patent Number: 4,782,187

[45] Date of Patent: Nov. 1, 1988

[54] PROCESS FOR THE PREPARATION OF 4,4'-STILBENEDIALDEHYDES

[75] Inventors: Dieter Reinehr, Kandern, Fed. Rep. of Germany; Heinz Steiner, Basel, Switzerland

[73] Assignee: Ciba-Geigy Corporation, Ardsley, N.Y.

[21] Appl. No.: 940,312

[22] Filed: Dec. 10, 1986

[30] Foreign Application Priority Data

Dec. 19, 1985 [CH] Switzerland ................ 5447/85

[51] Int. Cl.$^4$ .............................................. C07C 45/41
[52] U.S. Cl. ................................. 568/437; 568/434; 568/435
[58] Field of Search ............. 568/425, 426, 437, 435, 568/434

[56] References Cited

U.S. PATENT DOCUMENTS

| | | | |
|---|---|---|---|
| 3,517,066 | 6/1970 | Gurien et al. ................ | 568/435 |
| 3,847,989 | 11/1974 | Platz et al. ................ | 568/437 |
| 4,036,877 | 7/1977 | Petro et al. ................ | 568/437 |
| 4,240,984 | 12/1980 | de Witt et al. ................ | 568/438 |
| 4,420,433 | 12/1983 | Braden et al. ................ | 568/435 |
| 4,533,754 | 8/1985 | Gray ................ | 568/437 |

FOREIGN PATENT DOCUMENTS 0008123 2/1980 European Pat. Off. .
0104296 4/1984 European Pat. Off. .
1643639 7/1971 Fed. Rep. of Germany .

OTHER PUBLICATIONS

European Search Report.

*Primary Examiner*—Werren B. Lone
*Attorney, Agent, or Firm*—Kevin T. Mansfield; Edward McC. Roberts

[57] ABSTRACT

The preparation of 4,4'-stilbenedialdehydes from the corresponding acid chlorides in the presence of a noble metal catalyst.

20 Claims, No Drawings

PROCESS FOR THE PREPARATION OF 4,4'-STILBENEDIALDEHYDES

The present invention relates to a novel process for the preparation of 4,4'-stilbenedialdehydes of formula

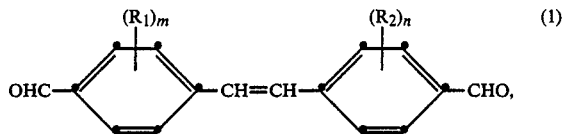

wherein $R_1$ and $R_2$ are each independently of the other substituents that cannot be reduced under the reaction conditions defined below, and m and n are each independently of the other 0, 1 or 2.

The process of this invention comprises hydrogenating compounds of formula

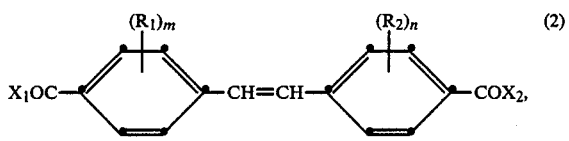

wherein $R_1$, $R_2$, m and n are as defined for formula (1) and $X_1$ and $X_2$ are each independently of the other hydrogen, chlorine or bromine, with the proviso that $X_1$ and $X_2$ are not simultaneously hydrogen, in an anhydrous, inert, aprotic organic solvent and in the presence of a noble metal catalyst, in the temperature range from 15° to 200° C. and under a pressure of 1 to 50 bar, until the absorption of a precalculated amount of hydrogen which is theoretically necessary to obtain the compound of formula (1), then separating the catalyst and isolating the compound.

Some of the compounds of formula (2) are known ($X_1$ and $X_2$ are simultaneously hydrogen, chlorine and bromine) amd some are novel ($X_1$ is hydrogen and $X_2$ is chlorine or bromine).

The invention thus further relates to novel compounds of formula (2) and to a process for the preparation thereof. The use of the compounds of formula (2) for the preparation of 4,4'-stilbenedialdehydes also falls within the scope of the invention.

In the compounds of formula (1), $R_1$ and $R_2$ are each independently of the other substituents that cannot be reduced under the reaction conditions applied in the process of the invention. For example, $R_1$ and $R_2$ are alkyl or alkoxy, each of preferably 1 to 4 carbon atoms, aryl or aryloxy, e.g. phenyl or phenoxy, halogen, preferably chlorine or bromine, or hydroxy, carboxyl or sulfo groups or derivatives of said groups, such as esters or amides.

The indices m and n are each independently of the other 0, 1 or 2, and are preferably both simultaneously 0.

In the compounds of formula (2), wherein $R_1$, $R_2$, m and n have the given meanings, $X_1$ and $X_2$ are each independently of the other hydrogen, chlorine or bromine, with the proviso that $X_1$ and $X_2$ are not simultaneously hydrogen. It is preferred that, in the compounds of formula (2), $X_1$ and $X_2$ are chlorine or $X_1$ is hydrogen and $X_2$ is chlorine.

In the process of this invention, the compounds of formula (2) are added to an anhydrous, aprotic organic solvent. Examples of suitable solvents are hydrocarbons or halogenated hydrocarbons, ketones, ethers, carboxylates, sulfones such as sulfolane, or mixtures of such solvents. Particularly suitable solvents are benzene, toluene, chlorobenzene, o-dichlorobenzene, acetone, dioxane, tetrahydrofuran and sulfolane, and mixtures thereof. The best results are obtained with o-dichlorobenzene.

A noble metal catalyst is required for carrying out the process of the invention. Preferred catalysts are platinum, palladium, iridium, rhodium, osmium or ruthenium or also nickel. Mixtures or alloys of these metals can also be used. Particularly good results are achieved with platinum and, especially, palladium.

The addition of a catalyst poison to the catalyst employed (partial poisoning) can be useful to prevent secondary reactions, especially the reduction of the central double bond as well as the overreduction of the formyl group to the corresponding alcohol or even hydrocarbon. To this end it is preferred to use sulfur-containing compounds, e.g. thiourea, 2-mercaptobenzthiazole or sulfur in quinoline (q.v. Ber. 54 (1921), 425).

The catalyst is usually applied to a carrier and normally in an amount of 0.5 to 25%. Examples of suitable carriers are activated carbon, barium and calcium sulfate, alumina and silica. The preferred carriers are activated carbon and barium sulfate.

In general, an amount of 5 to 25% of catalyst (including carrier), based on the substrate to be reduced, is employed in the process of this invention.

It can be advantageous to use an acid acceptor in the reaction solution to bind hydrogen halide formed during the hydrogenation. Hydrogen halide has the detrimental property of being able to deactivate the catalyst. Examples of suitable acid acceptors are bases such as N,N-dimethylaniline, N,N-dimethylacetamide, ethyl diisopropylamine, 2,6-dimethylpyridine, sodium acetate, magnesium oxide or sodium carbonate, with N,N-dimethylaniline, N,N-dimethylacetamide, ethyl diisopropylamine and 2,6-dimethylpyridine being particularly suitable. These preferred acid acceptors can simultaneously act as solvents.

Depending on the starting compound, solvent and catalyst, the reaction temperature and pressure may vary within wide limits. In general, the reaction temperature and pressure will be so chosen as to achieve an optimum ratio between the kinetics characteristic of a specific system of reactants (short reaction time) and selectivity (high yield of desired product).

A temperature range of 15° to 200° C., preferably of 70° to 140° C., and a pressure of 1 to 50 bar, preferably of 1 to 10 bar, have been found suitable for the process of the invention.

The process of this invention may be considered as terminated when a specific amount of hydrogen, which has been precalculated, has been absorbed by the reaction mixture. A precalculated amount of hydrogen shall be understood as meaning the theoretical amount of hydrogen required to obtain the compounds of formula (1) from the compounds of formula (2), which may contain one as well as two acid chloride groups.

The reaction time is normally from 30 minutes to 6 hours and working up of the reaction mixture is effected in a manner known per se. Upon removal of the catalyst, e.g. by filtration or centrifugation, the solvent is removed and the crude aldehyde is obtained in pure form, e.g. by distillation, recrystallisation, or formation of adducts with sodium bisulfite.

A preferred embodiment of the process of the invention comprises hydrogenating the compounds of formula (2), wherein $R_1$, $R_2$, m and n, $X_1$ and $X_2$ have the given meanings, in a mixture of o-dichlorobenzene and 2,6-dimethylpyridine and in the presence of a palladium catalyst which is partially poisoned with sulfur in quinoline, in the temperature range from 70° to 80° C. and under a pressure of 1.1 to 3 bar, until a precalculated amount of hydrogen has been absorbed by the reaction mixture.

The novel compounds of formula (2), wherein $X_1$ is hydrogen and $X_2$ is fluorine, chlorine or bromine, can also be obtained by reduction of those compounds of formula (2), wherein $X_1$ and $X_2$ are fluorine, chlorine or bromine. The hydrogenation of the starting compounds is discontinued when the theoretically calculated amount of hydrogen has been absorbed up by the reaction mixture.

Of these novel compounds, the compound of formula

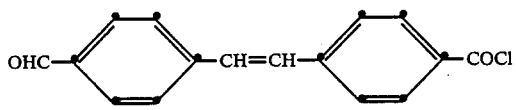

(3)

is especially preferred.

Preferably the reaction conditions described above are employed for the preparation of the novel compounds of formula (2) which contain a formyl and an acid halide group, as well as for the use of these compounds for the preparation of compounds of formula (1).

The compounds of formula (1) are useful intermediates for e.g. the synthesis of fluorescent whitening agents.

EXAMPLE 1

A hydrogenation flask (e.g. a Parr low pressure hydrogenation flask) is charged with 30.5 g (0.1 mole) of 4,4'-stilbenedicarboxylic acid chloride, 700 ml of o-dichlorobenzene (dried over phosphorus pentoxide) and 21.9 g of 2,6-dimethylpyridine. To this mixture are added 50 ml of o-dichlorobenzene, 6 g of palladium catalyst (barium sulfate carrier with 5% by weight of palladium) and 75 mg of quinoline-S (prepared in accordance with Ber. 54, (1921), 425). Hydrogenation is effected at 70° C. and 1.1 bar hydrogen pressure until 0.2 mole of hydrogen has been absorbed after 6 hours. The hydrogenation then comes to a virtual stop. Thereafter the catalyst is removed and the resultant salt is isolated by filtration from the reaction solution and evaporated to dryness, affording 17 g (72%) of almost pure 4,4'-stilbenedialdehyde with a melting point of 169°–171° C. The signals of the NMR and IR spectra are in conformity with the expected structure of the resultant compound.

Similar results are obtained by using a platinum instead of the palladium catalyst.

EXAMPLE 2

The procedure described in Example 1 is repeated, except for introducing only half the indicated amount of hydrogen and boiling the reaction solution with 500 ml of ethanol. Ethyl 4-formyl-4'-stilbenecarboxylate (derivative of 4-formyl-4'-stilbenecarboxylic acid chloride) is obtained by thin-layer chromatography.

EXAMPLE 3

The procedure of Example 2 is repeated, except for evaporating the reaction solution to dryness. The IR spectrum of the residue shows the expected signals of 4-formyl-4'-stilbenecarboxylic acid chloride.

What is claimed is:

1. A process for the preparation of a 4,4'-stilbenedialdehyde of formula

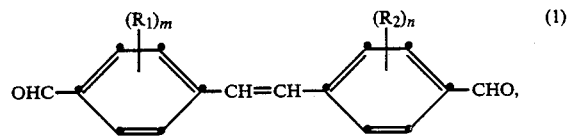

(1)

wherein $R_1$ and $R_2$ are each independently of the other alkyl or alkoxy, each of 1 to 4 carbon atoms, phenyl, phenoxy, chlorine or bromine; or are hydroxyl, carboxyl or sulfo groups or ester or amide derivatives thereof, and m and n are each independently of the other 0, 1 or 2, which process comprises hydrogenating a compound of formula

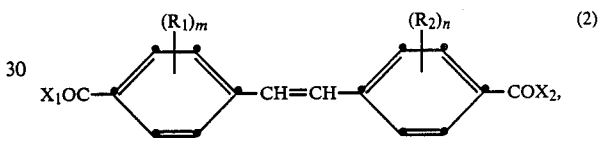

(2)

wherein $R_1$, $R_2$, m and n are as defined for formula (1) and $X_1$ and $X_2$ are each independently of the other hydrogen, chlorine or bromine, with the proviso that $X_1$ and $X_2$ are not simultaneously hydrogen, in an anhydrous, inert, aprotic organic solvent and in the presence of a noble metal catalyst, in the temperature range from 15° to 200° C. and under a pressure of 1 to 50 bar, until the absorption of a precalculated amount of hydrogen which is theoretically necessary to obtain the compound of formula (1), then separating the catalyst and isolating the compound.

2. A process according to claim 1, wherein the solvent is a hydrocarbon or halogenated hydrocarbon, a ketone, ether, carboxylate or sulfone, or a mixture of said solvents.

3. A process according to claim 1, wherein the solvent is benzene, toluene, chlorobenzene, o-dichlorobenzene, acetone, dioxane, tetrahydrofuran or sulfolane, or a mixture of said solvents.

4. A process according to claim 1, wherein the solvent is o-dichlorobenzene.

5. A process according to claim 1, wherein the noble metal catalyst is platinum, palladium, nickel, iridium, rhodium, osmium or ruthenium, or a mixture or alloy of said metals.

6. A process according to claim 5, wherein the noble metal catalyst is platinum or palladium.

7. A process according to claim 6, wherein the noble metal catalyst is palladium.

8. A process according to claim 5, wherein the noble metal catalyst is partially poisoned.

9. A process according to claim 8, wherein the catalyst poison is sulfur in quinoline, thiourea or 2-mercaptobenzthiazole.

10. A process according to claim 1, wherein the hydrogenation is carried out in the presence of an acid acceptor.

11. A process according to claim 10, wherein the acid acceptor is N,N-dimethylaniline, N,N-dimethylacetamide, ethyl diisopropylamine, 2,6-dimethylpyridine, sodium acetate, magnesium oxide or sodium carbonate.

12. A process according to claim 11, wherein the acid acceptor is N,N-dimethylaniline, N,N-dimethylacetamide, ethyl diisopropylamine or 2,6-dimethylpyridine.

13. A process according to claim 1, wherein the acid acceptor according to claim 12 is used as solvent.

14. A process according to claim 1, wherein the reaction temperature is in the range from 70° to 140° C.

15. A process according to claim 1, wherein the pressure is 1 to 10 bar.

16. A process according to claim 1, which comprises hydrogenating a compound of formula (2), wherein m and n are 0 and $X_1$ and $X_2$ are each independently of the other hydrogen, chlorine or bromine, with the proviso that $X_1$ and $X_2$ are not simultaneously hydrogen, in a mixture of o-dichlorobenzene and 2,6-dimethylpyridine and in the presence of a palladium catalyst which is partially poisoned with sulfur in quinoline, in the temperature range from 70° to 80° C. and under a pressure of 1.1 to 3 bar.

17. A process for the preparation of a compound of formula

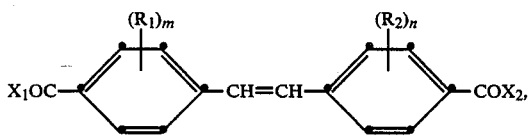

wherein $R_1$ and $R_2$ are each independently of the other alkyl or alkoxy, each of 1 to 4 carbon atoms, phenyl, phenoxy, chlorine or bromine; or are hydroxyl, carboxyl or sulfo groups or ester or amide derivatives thereof, m and n are each independently of the other 0, 1 or 2, $X_1$ is hydrogen and $X_2$ is chlorine or bromine, which comprises hydrogenating a compound of formula (2), wherein $R_1$, $R_2$, m and n have the given meanings and $X_1$ and $X_2$ are each independently of the other chlorine or bromine, in an anhydrous, inert, aprotic organic solvent and in the presence of a noble metal catalyst, in the temperature range from 15° to 200° C. and under a pressure of 1 to 50 bar, until the absorption of a precalculated amount of hydrogen, then separating the catalyst and isolating the compound.

18. A process according to claim 17 for the preparation of a compound of formula (2), wherein $X_1$ is hydrogen and $X_2$ is chlorine, which comprises hydrogenating a compound of formula (2), wherein m and n are 0 and $X_1$ and $X_2$ are chlorine, in a mixture of o-dichlorobenzene and 2,6-dimethylpyridine and in the presence of a palladium catalyst whch is partially poisoned with sulfur in quinoline, in the temperature range from 70° to 80° C. and under a pressure of 1.1 to 3 bar.

19. A compound of formula

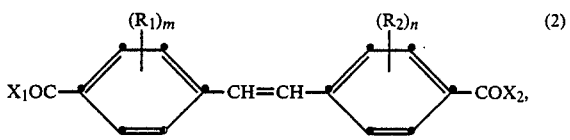

wherein $R_1$ and $R_2$ are each independently of the other alkyl or alkoxy, each of 1 to 4 carbon atoms, phenyl, phenoxy, chlorine or bromine; or are hydroxyl, carboxyl or sulfo groups or ester or amide derivatives thereof, m and n are each independently of the other 0, 1 or 2, $X_1$ is hydrogen and $X_2$ is chlorine or bromine.

20. A compound according to claim 19 of formula

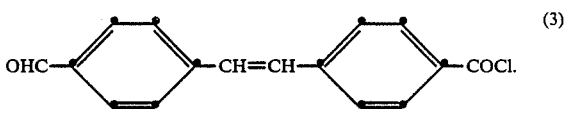

* * * * *